United States Patent [19]

Yang

[11] Patent Number: 5,474,757

[45] Date of Patent: Dec. 12, 1995

[54] PREVENTION OF ACETAMINOPHEN OVERDOSE TOXICITY WITH ORGANOSULFUR COMPOUNDS

[75] Inventor: Chung S. Yang, Bridgewater, N.J.

[73] Assignee: Rutgers University, Piscataway, N.J.

[21] Appl. No.: 962,529

[22] Filed: Oct. 16, 1992

[51] Int. Cl.$^6$ .................. A61K 49/00; A61K 31/195; A61K 31/16; A61K 31/10

[52] U.S. Cl. .................. 514/562; 514/625; 514/710; 514/823; 514/922

[58] Field of Search .................. 514/561, 62 C, 514/710, 922, 562, 625; 424/10

[56] References Cited

U.S. PATENT DOCUMENTS 4,307,073  12/1981  Nelson .................. 424/10
4,314,989  2/1982   Rosen .................. 424/10

OTHER PUBLICATIONS

The Handbook of Nonprescription Drugs, 8th edition, Published by The American Pharmaceutical Assn., (1986) pp. 153–161.

Brady et al., "Effect of Diallyl Sulfide on Rat Liver Microsomal Nitrosamine Metabolism and Other Monooxygenase Activities", Cancer Res. 48:5937–5940 (1988).

Brady et al., "Inhibition of Cytochrome P–450 2E1 by Dially Sulfide and its Metabolites", Chem. Res. Toxicol. 4:642–647 (1991).

Brady et al., "Effects of Disulfiram on Hepatic P450IIE1, Other Microsomal Enzymes, and Hepatotoxicity in Rats", Toxicol. Appl. Pharmacol. 108:366–373 (1991).

Yang, et al., "Cytochrome P450IIE1: Roles in Nitrosamine Metabolism and Mechanisms of Regulation", Drug Metab. Rev., 22:147–160 (1990).

Brady, et al., "Modulation of Rat Hepatic Microsomal Monooxygenase Enzymes and Cytotoxicity by Dially Sulfide", Toxicol. Appl. Pharm. 108, 342–354 (1991).

*Primary Examiner*—Raymond J. Henley, III
*Attorney, Agent, or Firm*—Steinberg, Raskin & Davidson

[57] ABSTRACT

A method of preventing acetaminophen (APAP)-induced hepatotoxicity utilizing diallyl sulfide (DAS) and diallyl sulfone (DASO$_2$) is disclosed. DAS and DASO$_2$ are prepared as an oral dosage form or injected. In a preferred embodiment, diallyl sulfone is added to a dosage form of acetaminophen in an amount effective to prevent the metabolism of said unit dose of acetaminophen into its hepatotoxic metabolites. In certain preferred embodiments, the above formulations further include an effective amount of N-acetylcysteine to detoxify hepatotoxic metabolites of acetaminophen.

25 Claims, 6 Drawing Sheets

PREVENTION OF ACETAMINOPHEN OVERDOSE TOXICITY WITH ORGANOSULFUR COMPOUNDS

This work was supported by NIH Grant ES-03938.

BACKGROUND OF THE INVENTION

Acetaminophen (APAP, N-acetyl-p-aminophenol, paracetamol) is the leading analgesic and antipyretic drug used in the United States. Acetaminophen is well tolerated, lacks many of the side effects of aspirin, and is available without prescription.

It is well-established that large acetaminophen overdose causes hepatotoxicity and in rare cases nephrotoxicity in humans and in experimental animals. Acute overdosage of acetaminophen results in dose-dependent and potentially fatal hepatic necrosis as well as in rare cases renal tubular necrosis and hypoglycemia.

At recommended dosages, most ingested acetaminophen is metabolized by sulfation and glucoronidation to form non-toxic metabolites which are excreted in the urine. A small percentage, generally estimated at less than 5%, is metabolized in the human liver by microsomal cytochrome P-450 to a metabolite, believed to be N-acetyl-p-benzoquinone imine (NAPQI). NAPQI bonds covalently to cellular constituents irreversibly arylating critical cellular proteins and causing cell death.

At therapeutic doses of acetaminophen, the small amount of NAPQI formed is detoxified prior to arylating cellular proteins by preferential conjugation or reaction with hepatic glutathione (via sulfhydryl groups). Subsequently, the detoxified NAPQI is excreted in the urine as conjugates of cysteine and mercapturic acid. However, when acetaminophen is taken in a large overdosage, glutathione stores may become depleted and hepatic necrosis may occur.

Recently, certain immunohistochemical studies have suggested that NAPQI-protein adducts appeared even at subhepatotoxic acetaminophen doses and before depletion of total hepatic glutathione. (Roberts et al., "Immunohistochemical Localization and Quantification of the 3-(cystein-S-yl)-Acetaminophen Protein Adduct in Acetaminophen Hepatotoxicity", Am. J. Pathol. 138:359–371 (1991)). It has been suggested that the formation of such NAPQI-protein adducts may be related to rare cases of hypersensitivity. (Stricker and Meyboom, "Acute Hypersensitivity Reaction to Paracetamol", Br. Med. J. 291:938–939 (1985); Hurvitz et al., "Acetaminophen Hypersensitivity Resembing Kawasaki Disease", Israel J. Med. Sci., 20:145–147 (1984)).

In the human liver, microsomal cytochromes P-450s 2E1 and 1A2 appear to be the two major enzymes responsible for the bioactivation of acetaminophen. (Raucy et al., "Acetaminophen Activation by Human Liver Cytochromes P450IIE1 and P450IA2", Arch. Biochem. Biophys. 271:270–283 (1989)). Studies in mouse kidney have also suggested that P-450 2E1 plays an important role in the bioactivation of acetaminophen (e.g., the conversion of acetaminophen to NAPQI (Hu et al., "Sex-Related Differences in Mouse Renal Cytochrome P450IIE1: Effects on the Metabolism and Nephrotoxicity of Acetaminophen, FASEB J 5:Abstract (1991)).

Early treatment of acetaminophen overdosage is considered to be crucial, and vigorous supportive therapy is essential when intoxication is severe. It is recommended that induction of vomiting or gastric lavage be performed in most cases when less than 24 hours has elapsed since overdose.

Protective agents for acetaminophen overdose have been extensively studied. A known method of treatment is the administration of sulfhydryl compounds. L-methionine, L-cysteine, and N-acetylcysteine are known to have a protective action in animals. Methionine and another sulfhydryl compound, cysteamine (possibly a source of sulfate for conjugation), have been reported to provide some protection (see, e.g., Prescott et al., "Cysteamine, Methionine, and Penicillamine in the Treatment of Paracetamol Poisoning", Lancet, 2:109–113 (1976)). N-acetylcysteine is considered to be effective when given orally. Also, cimetidine, dimethyl sulfoxide, and ethanol have been shown to inhibit acetaminophen bioactivation. Early administration of compounds supplying sulfhydryl groups (0 to 10 hours after acetaminophen ingestion) may prevent or minimize hepatic injury in cases of acetaminophen overdose.

The inventor has demonstrated that diallyl sulfide (DAS), a compound contained in garlic, is metabolized to diallyl sulfoxide (DASO) and diallyl sulfone ($DASO_2$) (Brady et al., "Inhibition of Cytochrome P-450IIE1 by Diallyl Sulfide and its Metabolites", Chem. Res. Toxicol. 4:642–647 (1991)). Treatment of rats with these compounds decreased liver microsomal P-450 2E1-dependent, e.g. N-nitrosodimethylamine (NDMA) demethylase, activity. The decrease by $DASO_2$ was found to occur more rapidly than by DAS or DASO (Brady et al., "Effect of Diallyl Sulfide on Rat Liver Microsomal Nitrosamine Metabolism and Other Monooxygenase Activities, Cancer Res. 48:5937–5940 (1988); Brady et al., "Modulation of Rat Hepatic Microsomal Monooxygenase Activities and Cytotoxicity by Diallyl Sulfide", Toxicol. Appl. Pharmacol. 108:342–354 (1991)). Furthermore, in isolated rat liver microsomes, DAS, DASO, and $DASO_2$ inhibited P-450 2E1-catalyzed (NDMA) demethylase and p-nitrophenol hydroxylase (e.g., p-nitrophenol hydroxylase) activities competitively, and $DASO_2$ also caused a metabolism-dependent inactivation (Brady et al., "Inhibition of Cytochrome P-450IIE1 by Diallyl Sulfide and its Metabolites", Chem. Res. Toxicol. 4:642–647 (1991)). DAS has also been shown to protect toxicity associated with carbon tetrachloride hepatotoxicity (Brady et al., "Modulation of Rat Hepatic Microsomal Monooxygenase Activities and Cytotoxicity by Diallyl Sulfide", Toxicol. Appl. Pharmacol. 108:342–354 (1991)), and 1,2-dimethylhydrazine-induced hepatotoxicity and carcinogenesis in rats (Hayes et al., "Inhibition of Hepatocarcinogenic Responses to 1,2-Dimethylhydrazine by Diallyl Sulfide, a Component of Garlic Oil" Carcinogenesis (Lond.) 8:1155–1157 (1987); Wargovich, "Diallyl Sulfide, a Flavor Component of Garlic (Allium Sativum), Inhibits Dimethylhydrazine-Induced Colon Cancer", Carcinogenesis (Lond.), 8:487–489 (1987)). It has been demonstrated that pre-treatment of rats with DAS, $DASO_2$ or disulfiram inhibited the hepatotoxicity of $CCl_4$ and N-nitrosodimethylamine; both are substrates of P450 2E1 (Yang, et al., "Cytochrome P450 2E1: Roles in Nitrosamine Metabolism and Mechanisms of Regulation", Drug Metab. Rev., 22:147–160 (1990)).

OBJECTS AND SUMMARY OF THE INVENTION

It is an object of the present invention to provide a method for the reduction of toxicity associated with acetaminophen overdose.

It is a further object of the present invention to provide compositions which are useful in the reduction of toxicity associated with acetaminophen overdose.

It is a further object of the present invention to provide a method and compositions which are useful in the prevention of hypersensitivities which occur in rare cases from, e.g., metabolic products of acetaminophen.

It is a further object of the present invention to provide strategies to reduce toxicity associated with acetaminophen overdose by inhibiting NAPQI formation.

It is a further object of the present invention to provide compositions which are useful in the protection against the toxicity of many small, volatile environmental chemicals which are metabolized by P450 2E1 into toxic metabolites.

These objects and others are achieved by the present invention, which relates to the use of diallyl sulfone ($DASO_2$), diallyl sulfoxide (DASO), diallyl sulfide (DAS), related compounds, and mixtures thereof, in the prevention of acetaminophen-induced toxicity associated with acetaminophen overdosing.

The present invention is related to the surprising discovery that DAS, DASO and $DASO_2$; are potent protective agents against hepatotoxicity associated with acetaminophen overdose.

In accordance with the above objects and others, an embodiment of the present invention is related to a method of treating acetaminophen overdose in a patient who has ingested an hepatotoxic dose of acetaminophen, comprising administering a protective agent comprising diallyl sulfone, diallyl sulfide, diallyl sulfoxide, related compounds, or mixtures thereof in an amount effective to prevent the metabolism of the ingested dose of acetaminophen into its hepatotoxic metabolites. The protective agent is administered as soon as possible after ingestion of the toxic dose of acetaminophen, e.g., within about 24 hours, and more preferably within about 3 hours, after the acetaminophen dose has been ingested, and most preferably concurrently or immediately after the overdose acetaminophen.

In certain preferred embodiments, a compound which supplies sulfhydryl groups, such as N-acetylcysteine, L-methionine, L-cysteine, mixtures thereof, etc. is also administered with the protective agent, in an effective amount to detoxify the hepatotoxic metabolites of acetaminophen.

The present invention is also related to a composition for treating an overdose of acetaminophen, comprising a pharmaceutically acceptable form of a protective agent comprising diallyl sulfone, diallyl sulfide, diallyl sulfoxide, or mixtures thereof, in an amount effective to prevent the metabolism of an ingested dose of acetaminophen into its hepatotoxic metabolites. In certain preferred embodiments, the composition further comprises an effective amount of N-acetylcysteine, L-methionine, L-cysteine, or mixtures thereof, to detoxify hepatotoxic metabolites of acetaminophen. The composition may be in an oral dosage form, or may be in a form suitable for injection.

The present invention is further related to a composition for treating acetaminophen overdose, comprising diallyl sulfone diallyl sulfide, or diallyl sulfoxide, preferably in an amount from about 0.1 mg/kg/day to about 100 mg/kg/day, based on patient weight.

One embodiment of the present invention is related to a method for the treatment of pain or fever with acetaminophen which reduces the formation of hepatotoxic metabolites, comprising administering to a human a therapeutically effective amount of acetaminophen and a protective agent selected from the group consisting of diallyl sulfone, diallyl sulfide, and mixtures thereof, in an effective amount to substantially inhibit the metabolism of the therapeutically effective amount of acetaminophen into a hepatotoxic metabolite.

Another preferred embodiment of the present invention is related to an oral dosage form comprising a pharmaceutically acceptable unit dose of acetaminophen, and a protective agent selected from the group consisting of diallyl sulfone, diallyl sulfide, diallyl sulfoxide, and a mixture thereof in an amount effective to substantially prevent the metabolism of the unit dose of acetaminophen into its hepatotoxic metabolites. This composition may be in a form in which acetaminophen is typically commercially available, e.g., elixirs, oral solutions, oral suspensions, drops, syrups, wafers, tablets, chewable tablets, gelcaps, caplets, capsules, suppositories, and buffered effervescent granules. In certain preferred embodiments, the composition may further comprise an effective amount of N-acetylcysteine to detoxify any hepatotoxic metabolites of the unit dose of acetaminophen.

In pre-manufactured compositions, the amount of diallyl sulfide, diallyl sulfone, and N-acetylcysteine may be based on, e.g., the average adult body weight of about 70 kg, and formulation concerns (e.g., size of the tablet).

In a further advantageous embodiment of the present invention, diallyl sulfone, diallyl sulfide, diallyl sulfoxide, related compounds and mixtures thereof are used in the protection against the toxicity of many small, volatile environmental chemicals which are metabolized by P450 2E1 to toxic metabolites.

BRIEF DESCRIPTION OF THE DRAWINGS

The following drawings are illustrative of embodiments of the invention and are not meant to limit the scope of the invention as encompassed by the claims.

DETAILED DESCRIPTION

It has now been surprisingly discovered that DAS, DASO, and $DASO_2$ administered after a toxic dosage of acetaminophen prevent the formation of hepatotoxic metabolites in mammals including humans.

It has furthermore been surprisingly discovered that the DAS, DASO and/or $DASO_2$ may also be administered with N-acetylcysteine to prevent the formation of hepatotoxic metabolite. Thus, in a further advantageous embodiment of the present invention, N-acetylcysteine is used concomitantly with DAS, $DASO_2$. Related compounds, may be included instead of part or all of the N-acetylcysteine.

It is hypothesized that the protective effects of DAS and $DASO_2$ are most probably due to the block of this metabolic activation through the inactivation and inhibition of cytochromes P-450 2E1 and perhaps other enzymes (which appear to be involved in the N-hydroxylation of acetaminophen which leads to the formation of NAPQI). However, this hypothesis is for discussion purposes only, and is not meant to limit the claims in any manner whatsoever.

The conventional oral dosage of acetaminophen is 325 mg to 1000 mg every 4 hours for adults and children 12 years of age and older (not to exceed 4 g in 24 hours). For young children, the single dose is 10–15 mg/kg/dose; total daily dosage should not exceed 60 mg/kg/day.

In adults, hepatotoxicity may occur after ingestion of a single dose of more than about 7.5 to 10 g of acetaminophen. Fatalities are rare with acute overdoses of less than 15 g. Alcoholics and individuals taking isoniazid have elevated P-450 2E1 levels and may have increased susceptibility for acetaminophen toxicity. The risk of hepatotoxicity with single toxic doses of acetaminophen may also be increased in patients regularly taking other hepatic enzyme-inducing agents, especially barbiturates or other anticonvulsants.

Symptoms during the first 2 days of acute poisoning by acetaminophen overdose do not reflect the potential seriousness of the intoxication. Nausea, vomiting, anorexia, and abdominal pain occur during the initial 24 hours and may persist for a week or more. The plasma acetaminophen half-life is prolonged in cases of hepatotoxicity, and is a useful predictor of hepatic necrosis. If plasma acetaminophen half-life exceeds 4 hours, hepatic necrosis is likely to occur. Likewise, plasma acetaminophen levels greater than 300 mcg/ml at 4 hours after ingestion, or greater than 50 mcg/ml at 12 hours, are always associated with hepatic damage. Hepatic damage may be clinically apparent within 2 to 6 days of ingestion of toxic doses. Initially, plasma transaminase and lactic dehydrogenase activity may be elevated. Different cell types contain unique combinations of enzymes; when these enzymes escape from dying cells into the blood stream, they provide valuable evidence about the cells that are affected. Most serum enzymes of clinical significance are intracellular in origin and are elevated in, e.g., injury to cardiac, hepatic, pancreatic, muscle, bone tissue. When cells die, macromolecules normally confined within the cells escape into the interstitial fluid and thence to the blood stream. Circulating enzyme levels do not rise when cellular damage is merely functional; therefore, cells that permit enzymes to enter the circulation have been damaged irreversibly.

In demonstrating liver damage, the principal enzymes are the transaminases, alkaline phosphatase, lactic dehydrogenase, leucine aminopeptidase, and gamma-glutamyl transpeptidase.

Transaminases catalyze the reversible transfer of amino groups between various acids in the glycolytic cycle. In human tissues, two have been recognized, and both have glutamic acid as one of the substrates. Glutamic-oxalacetic transaminase (GOT) mediates between glutamic and oxalacetic acid, and glutamic-pyruvic transaminase (GPT) has pyruvic acid as the other substrate. Kidney, heart, and skeletal muscle, in decreasing order, have significant concentrations of GPT. Liver contains the highest concentrations of GPT. Both colorimetric and spectrophotometric methods of assay are used, and normal serum values vary from laboratory to laboratory, depending upon the technique.

When hepatic cells are damaged, serum GOT and GPT levels rise. The enzyme levels are especially useful in assessing subtle or early changes. In hepatitis, for example, transaminase levels rise several days before jaundice begins. The enzyme levels also fall rapidly and may return to normal while parenchymal changes are still active. The serum GPT level returns to normal more slowly than does the GOT. Mild elevation occurs in cases of active cirrhosis.

Lactic dehydrogenase (LDH) catalyzes the reversible conversion between lactic and pyruvic acids. This reaction is important in nearly all mammalian cells, and large quantities of LDH exist in many tissues. Red and white blood cells, skeletal muscle, cardiac muscle, and liver are especially rich sources of LDH, and serum LDH levels rise if damage occurs to any of these cells. Different cell types contain the enzyme in subtly different forms, called isoenzymes, which can be exploited to pinpoint the cell of origin. Hepatic LDH moves slowly on electrophoresis and is readily inactivated by heat.

Serum LDH rises in most types of hepatocellular injury. For example, mild to moderate elevation occurs in all forms of hepatitis, in obstructive jaundice, and in cirrhosis.

It has now been surprisingly discovered that DAS and $DASO_2$ administered after a toxic dosage of acetaminophen prevent the development of hepatotoxicity, as indicated by serum glutamic-pyruvic transaminase (GPT) and lactate dehydrogenase (LDH) levels and by liver histopathology. The protection provided by N-acetylcysteine is similar, but however is only achieved at more than ten-fold higher dosages than that which is needed via the administration of DAS and $DASO_2$.

Although $DASO_2$ and DAS are preferred in certain embodiments of the present invention, other related chemicals, including diallyl sulfoxide (DASO) and Me-allyl sulfide, are also useful in the same manner to prevent the development of hepatotoxicity. Thus, in the compositions of the present invention, diallyl sulfoxide and Me-allyl sulfide, and other related compounds known to those skilled in the art, can be substituted for all or-part of the $DASO_2$ or DAS included therein. Such formulations are deemed to be encompassed by the appended claims.

It has furthermore been surprisingly discovered that the protective effects of $DASO_2$ (or DAS) and N-acetylcysteine are additive. Thus, in a further advantageous embodiment of the present invention, N-acetylcysteine is used concomitantly with DAS, $DASO_2$, related compounds, or mixtures thereof. Other compounds which supply sulfhydryl groups, such as, e.g., L-methionine, L-cysteine, and related compounds, may be included instead of part or all of the N-acetylcysteine.

It is hypothesized that the protective effects of DAS and $DASO_2$ are most probably due to the block of this metabolic activation through the inactivation and inhibition of cytochromes P-450 2E1 and 1A2, and perhaps other enzymes. However, this hypothesis is for discussion purposes only, and is not meant to limit the claims in any many whatsoever.

The protective effect of DAS and $DASO_2$ was demonstrated at a low dose of 5 mg/kg in both rats and mice. Furthermore, oral administration of $DASO_2$ was shown to cause rapid decreases of hepatic cytochromes P-450 2E1 and 1A2 activities in mice. With some exceptions, the results and serum GTP and LDH changes generally agreed with those based on histopathology. When given 1 or 3 hours after the acetaminophen dose, $DASO_2$ was more effective in protecting the hepatotoxicity of rats than of mice, possible due to a large GSH pool or a more efficient GSH generating system of the former than the latter. When $DASO_2$ was given at doses of 5, 15, or 50 mg/kg body weight to rats one hour after a high dose of acetaminophen (400 mg/kg), protection of hepatotoxicity was observed using serum glutamate-pyruvate transaminase and lactate dehydrogenase activities and the severity of liver necrosis as indicators. Partial protection was also observed when $DASO_2$ was given 3 or 6 hours after the acetaminophen treatment.

Toxic overdoses of acetaminophen in animals produce hepatic injury with histological features similar to those in man. Goodman & Gilman, "The Pharmacological Basis of Therapeutics" Sixth Edition, Chapter 29, page 704, ©1980 by MacMillan Publishing Co., Inc. Therefore, it is well-recognized in the art that the efficacy of preventative treatments for acetaminophen-induced hepatotoxicity in animals (e.g., rats and mice) is especially relevant to the use of such treatments in humans.

The present invention is advantageous over the prior art antidotes such as N-acetylcysteine alone because it prevents the initial formation of the toxic metabolite, NAPQI, in the treatment of acetaminophen overdoses. N-acetylcysteine is generally believed to work by stimulating the synthesis of glutathione (GSH), thus increasing cellular glutathione level which is decreased by toxic metabolites of acetaminophen, and increasing the formation of acetaminophen sulfate. However, N-acetylcysteine may not remove all of the toxic metabolite (NAPQI) that is produced. By preventing the formation of the toxic metabolite, the compositions of the present invention may also protect toxicity (such as hypersensitivity) which may not be protected by N-acetylcysteine. Surprisingly, the dose of N-acetylcysteine required to provide similar protection to $DASO_2$ is more than ten-fold higher than the dose of $DASO_2$.

DAS is a naturally occurring compound and is commercially available (e.g., from The Aldrich Chemical Co., Milwaukee, Wis., U.S.). $DASO_2$, a metabolite of the naturally occurring DAS, is non-volatile, odorless, chemically stable, requires low dosage, and can be taken orally. $DaSO_2$ is a commercially available product (e.g., from Parish Chemical Co., Orem, Utah, U.S.). $DaSO_2$ can be synthesized, e.g., by oxidizing diallyl sulfide with hot 30% hydrogen peroxide in glacial acetic acid, extracting by methylene chloride, concentrating by rotary evaporation, and purifying by vacuum distillation and silica gel chromatography.

DAS and $DaSO_2$ compounds of the present invention can be processed in accordance with conventional pharmaceutical methods to produce medicinal agents for administration to patients, e.g., mammals including humans.

These compounds can be employed in admixtures with conventional excipients, i.e., pharmaceutically acceptable organic or inorganic carrier substances suitable for parenteral or enteral application which do not deleteriously react with DAS and $DASO_2$. Suitable pharmaceutically acceptable carriers include but not limited to water, salt solutions, alcohols, gum arabic, vegetable oils, benzyl alcohols, polyethylene glycols, gelate, carbohydrates such as lactose, amylose or starch, magnesium stearate talc, silicic acid, viscous paraffin, perfume oil, fatty acid monoglycerides and diglycerides, pentaerythritol fatty acid esters, hydroxy methylcellulose, polyvinyl pyrrolidone, etc. The pharmaceutical preparations can be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like which do not deleteriously react with the DAS and $DASO_2$. They can also be combined where desired with other active agents, e.g., N-acetylcysteine, L-methionine and L-cysteine. For parenteral application, particularly oily or aqueous solutions, as well as suspensions, emulsions, or implants, including suppositories. Ampoules are convenient unit dosages. For oral application, particularly suitable are tablets, dragees, liquids, drops, suppositories, or capsules, caplets and gelcaps. A syrup, elixir, or the like can be used wherein a sweetened vehicle is employed.

Sustained or direct release compositions can be formulated, e.g., liposomes or those wherein the active compound is protected with differentially degradable coating, e.g., by microencapsulation, multiple coatings, etc. It is also possible to freeze-dry the new compounds and use the lyphilizates obtained, for example, for the preparation of products for injection. Oral administration is currently preferred mode of administration.

Generally, the DAS and $DASO_2$ compounds of this invention are dispensed in unit dosage form comprising about 0.5–50 mg in a pharmaceutically acceptable carrier per unit dosage. The dosage of the DAS and/or $DASO_2$ according to this invention generally is 0.01–100 mg/kg/day, preferably 1–10 mg/kg/day and most preferably, from 1–5 mg/kg/day when administered to patients, e.g., humans to treat acetaminophen toxicity. It will be appreciated that the actual preferred amounts of active compound in this specific case will vary according to the particular composition formulated the mode of application and a particular situs and organism being treated. Dosages for a given host can be determined using conventional considerations e.g., by monitoring serum and liver enzymes levels (including but not limited to glutamic-pyruvic transaminase (GPT), glutamic-oxalacetic transaminase (GOT), and lactic dehydrogenase (LDH). It is currently preferred in the treatment of acetaminophen overdosages that DAS, $DASO_2$ and combinations thereof should be administered as soon as possible after the overdose of acetaminophen is discovered. Administration of these protective agents should generally begin within 24 hours after the overdose is discovered and preferably will begin less than 10 hours after the overdose is discovered and most preferably less than 6 hours after the overdose is discovered. The treatment with these protective agents should continue until a serum level of acetaminophen and liver enzyme levels return to acceptable levels, and if needed for several days thereafter. This period will generally vary from patient to patient depending on the severity of the overdose that can be generally monitored by following acetaminophen serum levels and serum and liver enzyme profiles.

N-acetylcysteine, L-methionine and L-cysteine may also be administered before, concomitantly with or after DAS and/or $DASO_2$ to treat acetaminophen overdosages. N-acetylcysteine, L-methionine and L-cysteine is considered to be effective when administered orally less than 24 hours after the overdose of acetaminophen. Generally, a loading dose 140 mg/kg of N-acetylcysteine is given, followed by the administration of 70 mg/kg every 4 hours or 17 doses. N-acetylcysteine administration is terminated if assays of acetaminophen in plasma indicate the risk of hepatotoxicity is low. N-acetylcysteine U.S.P. (Mucomyst) is commercially available as a sterile 10 or 20% solution and can be diluted with carbonated beverages, fruit juices or water to achieve a 5% solution. The generally recommended dosage of L-methionine is 2.5 g immediately, followed by 2.5 g at 4 hour intervals. When given concomitantly with DAS and/or $DASO_2$, etc., the dose of N-acetylcysteine may be reduced by one-third to one-half of the above-mentioned dose. When given concomitantly with DAS and/or $DASO_2$, etc., the dose of L-methionine may be from about 50 mg/kg/day to about 500 mg/kg/day.

In another preferred embodiment of the present invention, diallyl sulfide and/or diallyl sulfone is added to an effective dose of acetaminophen to provide analgesia, and the above ingredients, with one or more inert pharmaceutically acceptable excipients (optional), are manufactured in a pharmaceutically acceptable oral dosage form. The protective agent is included in the composition in an amount effective to prevent the metabolism of small amounts of the ingested dose of acetaminophen into its hepatotoxic metabolites.

Acetaminophen is commercially available in numerous oral dosage form. In one embodiments of the present invention, effective amounts of diallyl sulfide and/or diallyl sulfone is added to these oral dosage forms.

Various oral dosage forms can be used, including such solid forms as tablets, gelcaps, capsules, caplets, granules, lozenges and bulk powders and liquid forms such as emulsions, solution and suspensions. In the hospital setting, it may be most advantageous for these compositions to be in injectable form for the treatment of acute acetaminophen overdose.

Tablets can be compressed, tablet triturates, enteric-coated, sugar-coated, film-coated, multiply compressed or multiply layered containing suitable binder, lubricants, diluents, disintegrating agents, coloring agents, flavoring agents, preservatives and flow-inducing agents.

Liquid oral dosage forms include aqueous and nonaqueous solutions, emulsions, suspensions, and solutions and/or suspensions reconstituted from non-effervescent granules, containing suitable solvents preservatives, emulsifying agents, suspending agents, diluents, sweeteners, coloring agents, and flavorings agents.

Specific examples of pharmaceutically acceptable carriers and excipients that may be used to formulate oral dosage forms, are described in the *Handbook of Pharmaceutical Excipients*, American Pharmaceutical Association (1986), incorporated by reference herein. Techniques and compositions for making solid oral dosage forms are described in *Pharmaceutical Dosage Forms: Tablets* (Lieberman, Lachman and Schwartz, editors) 2nd edition, published by Marcel Dekker, Inc,. Incorporated by reference herein. Techniques and compositions for making tablets (compressed and molded), capsules (hard and soft gelatin) and pills are also described in *Remingtons's Pharmaceutical Sciences* (Arthur Oxol, editor), 1553–1593 (1980), incorporated herein by reference. Techniques and composition for making liquid oral dosage forms are described in *Pharmaceutical Dosage Forms: Disperse Systems*, (Lieberman, Rieger and Banker, editors) published by Marcel Dekker, Inc., incorporated herein by reference.

More particularly, the present invention relates to compositions of acetaminophen in oral solid unit doses of, e.g., 80 mg (for pediatric doses), 325 mg, 500 mg, and 650 mg together with effective amounts of diallyl sulfide and/or diallyl sulfone. The present invention is further related to suppositories comprising, e.g., 120 mg, 125 mg, 325 mg, 500 mg and 650 mg acetaminophen together with effective amounts of diallyl sulfide and/or diallyl sulfone. The present invention is further related to oral liquid dosage forms comprising, e.g., 100 mg/ml, 120 mg/2.5 ml, 120 mg/5 ml, 160 mg/5 ml, 165 mg/5 ml, 325 mg/5 ml acetaminophen together with effective amounts of diallyl sulfide and/or diallyl sulfone. The present invention is further directed to effervescent granules comprising, e.g., 325 mg acetaminophen, 2.781 g sodium bicarbonate, together with effective amounts of diallyl sulfide and/or diallyl sulfone.

In certain further preferred embodiments of the present invention, an effective amount an agent selected from N-acetylcysteine, L-cysteine, L-methionine, and combinations thereof, etc. is also included in the above-mentioned acetaminophen formulations.

Generally the amount of diallyl sulfone and/or diallyl sulfide used in formulations with acetaminophen will be an amount effective to substantially reduce or prevent the formation of the small amounts of NAPQI that may be formed on the administration of pharmaceutically acceptable dosages of acetaminophen. The appropriate amount of diallyl sulfone and/or diallyl sulfide may be empirically determined by monitoring liver and serum enzyme levels or monitoring the levels of conjugate hepatic glutathione. The amount of diallyl sulfone and/or diallyl sulfide used in formulations with acetaminophen is preferably from about 0.04 mg/kg/day to about 50 mg/kg/day.

Acetaminophen formulations for the purpose of this invention can also contain therapeutic amounts of other pharmaceutical actives conventionally employed with acetaminophen including but not limited to decongestants or bronchodilators (such as pseudoephedrine, phenylpropanolamine, phenylephrine and pharmaceutically acceptable salts thereof), antitussives (such as caraminophen, dextromethorphan and pharmaceutically acceptable salts thereof), antihistamines (such as chlorpheniramine, brompheniramine, dexchlorpheniramine, dexbromphreniramine, triprolidine, doxylamine, tripelennamine, cyproheptadine, pyrilamine, hydroxyzine, promethazine, azatadine and pharmaceutically acceptable salts thereof), non-sedating antihistamines (such as acrivastine, astemizole, cetirizine, ketotifen, loratidine, temelastine, terfenadine (including the metabolites disclosed in U.S. Pat. Nos. 4,254,129 and 4,284,957 hereby incorporated by reference and pharmaceutically acceptable salts thereof), muscle relaxants (such as glycerylmonether SMRS, methocarbamol, mephenesin, mephenesin carbamate, cyclobenzaprine, chlorzoxazone, mephenesin acid succinate, chlorphenesin carbamate, or pharmaceutically acceptable salts thereof) and suspected adjuvants (such as diphenhydramine, caffeine, xanthine derivatives (including those disclosed in U.S. Pat. No. 4,558,051, hereby incorporated by reference) and pharmaceutically acceptable salts thereof) and combinations of any of the aforesaid pharmaceuticals. The aforesaid pharmaceuticals may be combined with acetaminophen for the treatment of allergies, cough, colds, cold-like and/or flu symptoms in mammals including humans. However, these pharmaceuticals maybe combined with acetaminophen as sleep aids (such as diphenhydramine), or for other known purposes.

In a further advantageous embodiment of the present invention, DAS, $DASO_2$, related compounds, or mixtures thereof are used in the protection against the toxicity of many small, volatile environmental chemicals which are metabolized by P450 2E1.

DETAILED DESCRIPTION OF PREFERRED EMBODIMENTS

The following examples illustrate various aspects of the present invention. They are not to be construed to limit the claims in any manner whatsoever.

METHODS

The following materials, and methods for blood samples, microsome preparation, enzyme assays, histological examination, and statistics were used in the examples set forth below.

Materials

Diallyl sulfide was purchased from Aldrich Chemical Co. (Milwaukee, Wis.) Diallyl sulfone was purchased from Parish Chemical Co. (Orem, Utah) and purified by vacuum distillation; the purity was >99% as determined by gas chromatography. Acetaminophen and N-acetyl-L-cysteine were obtained from Sigma Chemical Co. (St. Louis, Mo.).

Blood Samples, Microsome Preparation, and Enzyme Assays.

Blood samples were obtained from the jugular vein of $CO_2$-anesthetized animals. The blood was allowed to clot at room temperature and serum was separated by centrifugation. Serum glutamic-pyruvic transaminase (GPT) and lactate dehydrogenase (LDH) activities as well as creatinine and total bilirubin levels were determined according to Sigma Procedures No. 505, 228, 557, and 605, respectively. Liver microsomes were prepared and N-nitrosodimethylamine demethylase activity was determined by a spectrophotometric method (Peng et al., "The Induction and Competitive Inhibition of a High Affinity Microsomal Nitrosodimethylamine Demethylase by Ethanol", Carcinogenesis (Lond.) 3:1457–1461 (1982); Brady et al., "Effect of Diallyl Sulfide on Rat Liver Microsomal Nitrosamine Metabolism and other Monooxygenase Activities", Cancer Res. 48:5937–5940 (1988)). pentoxyresorufin and ethoxyresorufin dealkylase assays were carried out by the fluorometric method of Lubet et al., Arch. Biochem. Biophys. 238:42–48 (1985).

Histological Examination

Randomly-selected samples of the major hepatic lobe were fixed in 10% buffered formalin for histological evaluation. Samples were subsequently embedded in Paraplast (Fisher Scientific) and sectioned at 6 μm on a rotary microtome. Tissue sections were stained with hematoxylin-eosine-phloxine for examination. Extent of tissue damage was determined using a Presage CV-6 Image Analysis System (Advanced Imaging Concepts, Inc.). Images of randomly-selected slides (3 slides/animal, 2–3 animals/group) containing full cross sections of the major hepatic lobe were projected onto a computer screen and the image captured. The areas of damage were then outlined on the screen and the areas quantated using interactive software. The area of damage was shown as a percentage of the total hepatic area for each section. All determinations were made without knowledge of treatment group.

Statistics

Data were analyzed by the Newman-Keuls multiple comparison procedure on the rank score analysis.

EXAMPLE 1

Protective Effect in Rats

In Examples 1a–1g, the protective effect of $DASO_2$ against acetaminophen overdose in rats was investigated.

Male Fisher 344 rats (80–90 g) were obtained from Taconic Farms (Germantown, N.Y.). They were maintained in temperature-controlled quarters with 12 hours light-dark cycles and with food and water ad libitum. Food was removed 16 hours prior to acetaminophen dosing and withheld for an additional 8 hours following treatment. Acetaminophen was suspended in 0.5% tragacanth (Sigma Co.) and given by gavage in a volume of 1 ml/100 g body weight. DAS in corn oil, or $DASO_2$ or N-acetylcysteine in distilled water, was administered orally in a volume of 1 ml/100 g body weight at indicated time points after APAP dosing. Animals were sacrificed 24 hours after APAP treatment. All experiments were replicated at least once.

In Example 1a, a 50 mg/kg dose of $DASO_2$ was given to a rat 1 hour after administration of 0.4 g/kg acetaminophen. In Example 1b, a 50 mg/kg dose of DAS was administered 1 hour after administration of 0.4 g/kg acetaminophen. In Example 1c, a 5 mg/kg dose of $DASO_2$ was given to a rat 1 hour after administration of 0.4 g/kg acetaminophen. In Example 1d, a 15 mg/kg dose of $DASO_2$ was given to a rat 1 hour after administration of 0.4 g/kg acetaminophen. As a Comparative Example, 600 mg/kg N-acetylcysteine was also given 1 hour after administration of 0.4 g/kg acetaminophen.

Each of Examples 1e–1g were given 3 hours after administration of 0.4 g/kg acetaminophen. In Example 1e, a 50 mg/kg dose of $DASO_2$ was administered. In Example 1f, a 5 mg/kg dose of $DASO_2$ was administered. In Example 1g, 5 mg/kg dose of $DASO_2$ and 50 mg/kg N-acetylcysteine were administered. As a Comparative Example, 50 mg/kg N-acetylcysteine was also administered 3 hours after administration of 0.4 g/kg acetaminophen.

Each of Examples 1h–1i were given 6 hours after administration of 0.4 g/kg acetaminophen. In Example 1h, a 50 mg/kg dose of $DASO_2$ was administered. In Example 1i, 5 mg/kg dose of $DASO_2$ and 600 mg/kg N-acetylcysteine were administered. As a Comparative Example, 50 mg/kg N-acetylcysteine was also administered 6 hours after administration of 0.4 g/kg acetaminophen.

The results of tests conducted as detailed in the "Methods" section above are set forth in Tables 1 and 2 below.

TABLE 1

Comparative Effects of $DASO_2$ and other Agents in Acetaminophen Overdose in Rats[a]

| Treatment | GPT* U/L | LDH** U/L | Extent of liver damage[d] |
|---|---|---|---|
| Control | 43 ± 5[b] | 235 ± 75[b] | 0% |
| APAP only | 206 ± 5[c] | 1568 ± 548[c] | 54–81% |
| 1 hour after APAP | | | |
| $DASO_2$, 50 mg/kg | 48 ± 9[b] | 279 ± 50[b] | 0–5% |
| N-AC, 600 mg/kg | 47 ± 4[b] | 174 ± 35[b] | 1–5% |
| DAS, 50 mg/kg | 70 ± 13[b] | 220 ± 82[b] | 5–13% |
| 3 hours after APAP | | | |
| $DASO_2$, 50 mg/kg | 133 ± 64[c] | 315 ± 120[b] | 4–8% |
| $DASO_2$, 5 mg/kg | 139 ± 46[c] | nd | 23–38% |
| N-AC, 50 mg/kg | 135 ± 40[c] | nd | 17–38% |
| $DASO_2$, 5 mg/kg+ N-AC***, 50 mg/kg | 91 ± 42[b] | nd | 0–4% |
| 6 hours after APAP | | | |
| $DASO_2$, 50 mg/kg | 182 ± 47[c] | 375 ± 111[b] | 21–40% |
| N-AC, 600 mg/kg | 153 ± 62[c] | 269 ± 92[b] | 13–28% |
| $DASO_2$, 50 mg/kg+ N-AC, 600 mg/kg | 176 ± 51[c] | 182 ± 57[b] | 19–22% |

[a]Rats were fasted for 16 hours prior to administration of 0.4 g/kg of APAP and treated under conditions indicated. Values represent mean ± SD of five rats in duplicate determination; nd, not determined.
[b-c]Means showing different superscripts in each column of each experiment are significantly different (p < 0.05) in the Newman-Keuls test.
[d]For purpose of comparison, extent of necrosis was graded by the criteria given in "Methods."
*GPT = glutamic-pyruvic transaminase.

TABLE 1-continued

Comparative Effects of $DASO_2$ and other Agents in Acetaminophen Overdose in Rats[a]

| Treatment | GPT* U/L | LDH** U/L | Extent of liver damage[d] |
|---|---|---|---|

**LDH = lactate dehydrogenase.
***N-AC = N-acetylcysteine

TABLE 2

Effects of $DASO_2$ Dosage and Treatment Time of Acetaminophen Overdose in Rats[a]

| $DASO_2$ mg/kg | Treatment time (h after) | GPT U/L | LDH U/L | Extent of liver necrosis[d] |
|---|---|---|---|---|
| 0 | 1 | 206 ± 5.3[b] | 1568 ± 548[b] | 3 |
| 5 | 1 | 162 ± 27.3[b] | 377 ± 71[c] | 1 |
| 15 | 1 | 52 ± 8.2[c] | 222 ± 44[c] | 1 |
| 50 | 1 | 48 ± 9.6[c] | 279 ± 41[c] | 0 |
| 50 | 3 | 133 ± 64[b] | 315 ± 120[c] | 1 |
| 50 | 6 | 182 ± 47[b] | 375 ± 111[c] | 2 |
| No APAP, no $DASO_2$ | | 43 ± 5.2[c] | 235 ± 75[c] | 0 |

[a]Rats were fasted for 16 hours prior to administration of 0.4 g/kg of APAP and treated with various amounts of $DASO_2$ at indicated time after APAP administration. Values represent mean ± SD of five rats in duplicate determinations.
[b-c]Means showing different superscripts in each column of each experiment are significantly different ($p < 0.01$) in the Newman-Keuls test.
[d]For purpose of comparison, extent of necrosis was graded by the criteria given in "Methods."

Figure 1A:
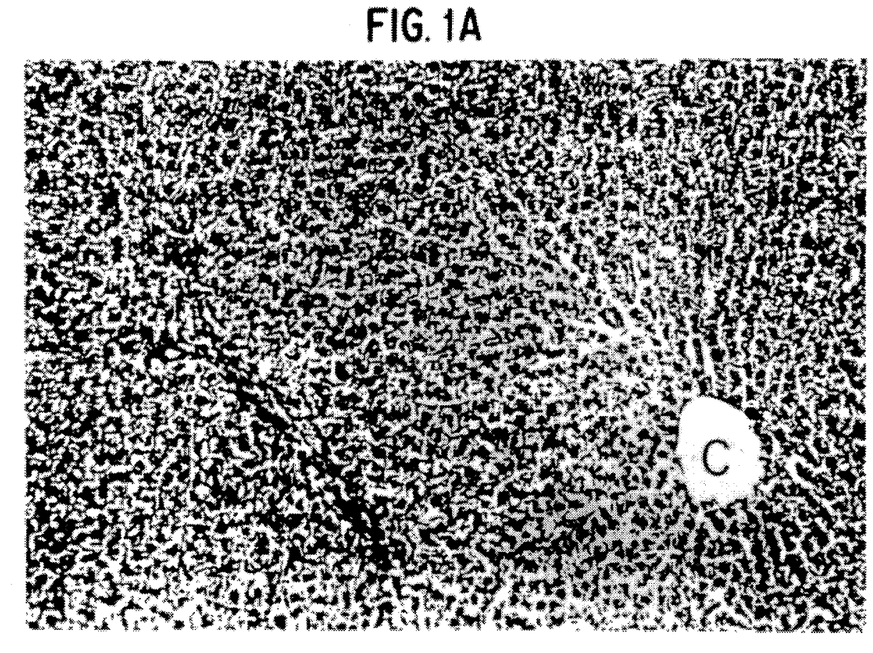
FIGS. 1A–1D are paraffin sections stained with hematoxy-lin-eosin-phloxine, x200, illustrating the effects of $DASO_2$ on acetaminophen-induced hepatotoxicity in rats.
Figure 1B:
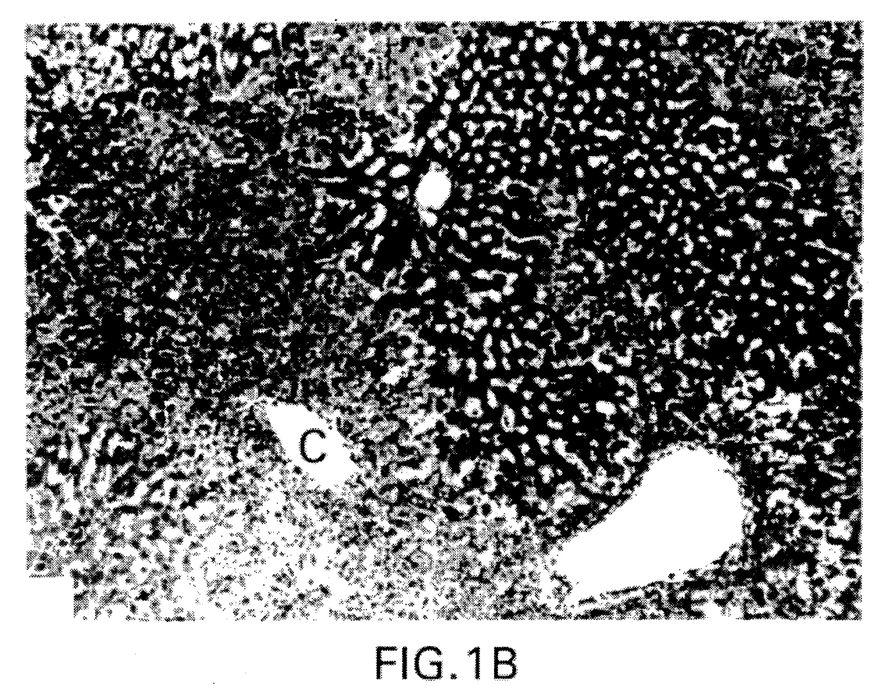
Figure 1C:
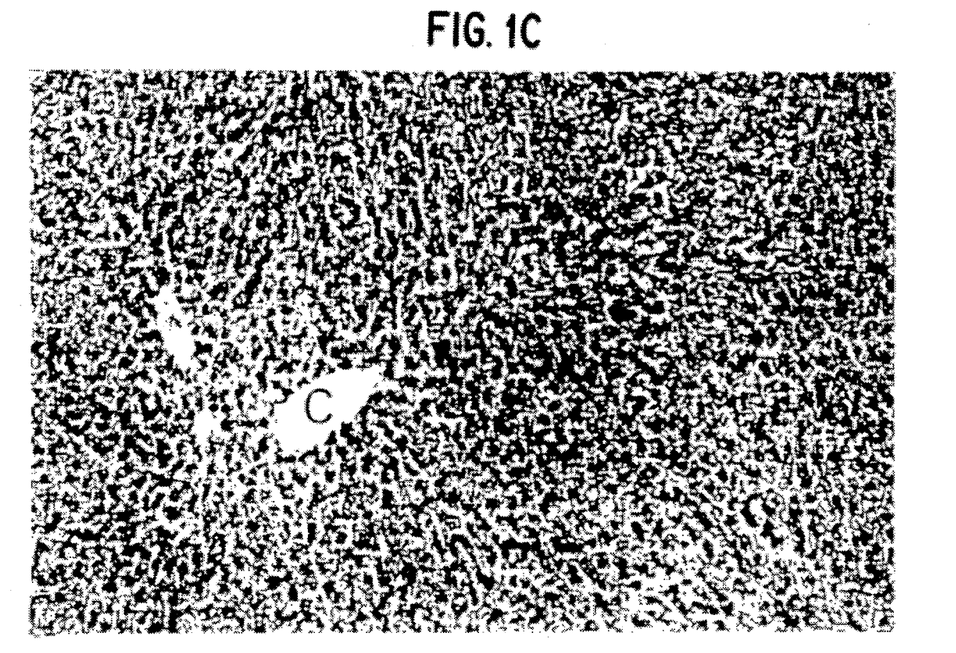
Figure 1D:
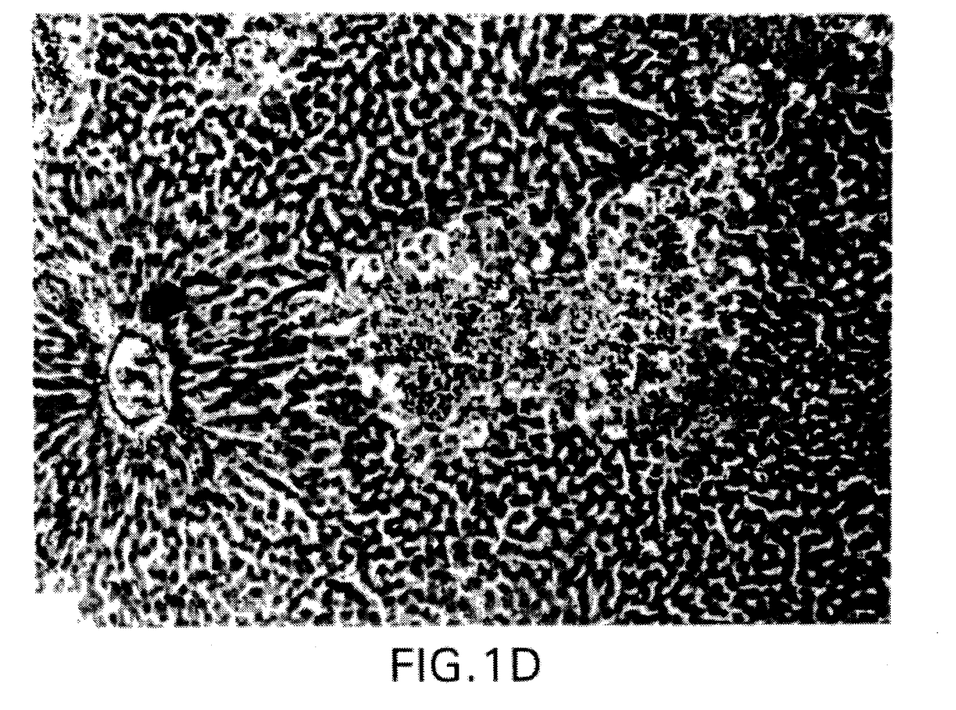

In FIGS. 1A–1D, paraffin sections stained with hematoxylin-eosin-phloxine, x200, the effects of $DASO_2$ on acetaminophen overdose in rats are illustrated. FIG. 1A is a control liver demonstrating patent central veins (C) and normal cords of hepatocytes. FIG. 1B is a liver section from a rat given acetaminophen (0.4 g/kg). Large areas of hepatocellular degeneration and necrosis are centered around the central vein (C). Hepatocytes surrounding the portal triad (arrow) are significantly less involved. FIG. 1C is a liver section from a rat given $DASO_2$ (50 mg/kg) 1 hour after acetaminophen (0.4 g/kg). Hepatic cytoarchitecture is essentially unremarkable. FIG. 1D is a liver section from a rat given $DASO_2$ 3 hours after acetaminophen (0.4 g/kg) administration. Mild to moderate hepatocellular damage is noted around the central veins. Inflammation, consisting of polymorphonuclear leukocytes and macrophages, is pronounced in the zone of necrotic tissue. Regions surrounding the portal triad (arrow) are uninvolved.

As can be ascertained from the results set forth above, an oral dose of APAP (0.4 g/kg) caused hepatotoxicity in rats which was indicated by elevated levels of serum GPT (5-fold increase) and LDH (7-fold increase) 24 hours after APAP treatment. No increase of serum creatinine was observed. Histological evaluation of liver damage caused by acetaminophen overdose showed that 54–80% of the liver was damaged, with large necrotic zones in the centralobular region. Fragmentation and dissolution of hepatocytes and infiltration of inflammatory cells (predominantly polymorphonuclear neutrophilic leukocytes and macrophages) were frequent (FIG. 1B). When 50 mg/kg of $DASO_2$ was given to rats 1 hours after APAP dosing, a protective effect was found and the liver morphology (FIG. 1C) was virtually indistinguishable from that of normal rats (FIG. 1A).

$DASO_2$ protected against acetaminophen overdose in a dose-and time-dependent manner as shown by its ability to prevent the elevation of serum GPT and LDH levels and the development of liver damage (Tables 1 and 2). At a dose as low as 5 mg/kg, when given 1 hr after acetaminophen administration, $DASO_2$ significantly prevented the elevation of serum LDH level and the development of severe liver damage. When 50 mg/kg $DASO_2$ was given 1 hr after acetaminophen dosing, it almost completely prevented hepatotoxicity; the rats had normal serum GPT and LDH levels and normal liver morphology. When given 3 and 6 hr after APAP, $DASO_2$ exhibited partial protection, as indicated by a lesser degree of hepatocellular damage and a normal LDH level; however, the GPT level remained high (FIG. 1D, Table 2).

Effects of treatments with $DASO_2$ and other compounds in rats. As shown in Table 2, N-AC (600 mg/kg), when given 1 hr after acetaminophen dosing, was as effective as $DASO_2$ (50 mg/kg) in preventing liver toxicity. Treatment with DAS prevented the elevation of serum GPT and LDH levels, but did not completely prevent liver damage. In Example 1g, submaximal dosages of $DASO_2$ (5 mg/kg) and N-AC (50 mg/kg) were given individually and in combinations to rats 3 hours after acetaminophen dosing. Each of the individual compound partially prevented the development of liver necrosis and the elevation of the GPT level, but the combination treatment completely prevented liver toxicity. The results suggest that the antidotal effects of $DASO_2$ and N-AC are additive. When given to rats 6 hours after acetaminophen dosing, $DASO_2$ (50 mg/kg) and N-AC (600 mg/kg) each provided partial protection (Example 1i). Both treatments lowered the serum LDH level, but they did not reduce the GPT level and liver damage very effectively. The combined treatment with $DASO_2$ and N-AC was not more effective, suggesting that irreversible liver damage had already occurred at 6 hours after APAP dosing.

EXAMPLE 2

Protective Effect in Mice

In Examples 2a–2g, the protective effect of $DASO_2$ against acetaminophen overdose in rats was investigated.

Male Swiss Webster mice (30–35 g, 8–10 week old) were obtained from Taconic Farms (Germantown, N.Y.). They were maintained in temperature-controlled quarters with 12 hours light-dark cycles and with food and water ad libitum. Food was removed 16 hours prior to APAP dosing and withheld for an additional 8 hours following treatment. Acetaminophen was suspended in 0.5% tragacanth (Sigma Co.) and given by gavage in a volume of 1 ml/100 g body weight. DAS in corn oil, or $DASO_2$ or N-acetylcysteine in distilled water, was administered orally in a volume of 1 ml/100 g body weight at indicated time points after APAP dosing. Animals were sacrificed 24 hours after APAP treatment. All experiments were replicated at least once.

Each of Examples 2a–2e were administered immediately after administration of 0.2 g/kg acetaminophen. In Example 2a, a 50 mg/kg dose of $DASO_2$ was administered. In Example 2b, 25 mg/kg of $DASO_2$ and 300 mg/kg N-acetylcysteine were administered. In Example 2c, a 25 mg/kg dose of DAS was administered. In Example 2d, a 5 mg/kg dose of $DASO_2$ was administered. In Example 2e, a 50 mg/kg dose of $DASO_2$ was administered. As a Comparative Example, 300 mg/kg N-acetylcysteine was also administered immediately after administration of 0.2 g/kg acetaminophen.

In Example 2f, a 25 mg/kg dose of $DASO_2$ was administered 20 minutes after administration of 0.2 g/kg acetaminophen. In Example 2g, a 25 mg/kg dose of DAS was administered 20 minutes after administration of 0.2 g/kg acetaminophen.

Each of Examples 2h–2j were given 1 hour after administration of 0.2 g/kg acetaminophen. In Example 2h, a 25 mg/kg dose of $DASO_2$ was administered. In Example 2i, 25 mg/kg dose of $DASO_2$ and 300 mg/kg N-acetylcysteine were administered. In Example 2j, a 25 mg/kg dose of DAS was administered. As a Comparative Example, 300 mg/kg N-acetylcysteine was also administered 1 hour after administration of 0.2 g/kg acetaminophen.

The results of tests conducted as detailed in the "Methods" section above are set forth in Tables 3 and 4 below.

TABLE 3

Comparative Effects of $DASO_2$ and other Agents in Acetaminophen Overdose in Mice[a]

| Treatment | Survival | GPT U/L | LDH U/L | Extent of liver damage[d] |
|---|---|---|---|---|
| Control | 5/5 | 66 ± 8[b] | 647 ± 236[b] | 0% |
| APAP only | 2/5 | 208 ± 5[c] | 17227 ± 3464[c] | 26–40% |
| Immediately after APAP | | | | |
| Control | 5/5 | 45 ± 20[b] | 541 ± 140[b] | 0% |
| $DASO_2$, 5 mg/kg | 5/5 | 51 ± 8[b] | 433 ± 98[b] | 3–5% |
| $DASO_2$, 25 mg/kg | 5/5 | 66 ± 18[b] | 611 ± 252[b] | 5–10% |
| N-AC, 300 mg/kg | 5/5 | 56 ± 4[b] | 629 ± 124[b] | 0% |
| $DASO_2$, 25 mg/kg + N-AC, 300 mg/kg | 5/5 | 60 ± 8[b] | 470 ± 101[b] | 0% |
| $DASO_2$, 50 mg/kg | 5/5 | 79 ± 5[b] | 772 ± 1138[b] | 4–9% |
| DAS, 25 mg/kg 20 min after APAP | 5/5 | 143 ± 50[c] | 1899 ± 1724[b] | 8–17% |
| 0 | 2/5 | 208 ± 5[c] | 14904 ± 5477[b] | nd |
| $DASO_2$, 10 mg/kg | 5/5 | 212 ± 1[c] | 16639 ± 8578[b] | nd |
| $DASO_2$, 25 mg/kg | 5/5 | 89 ± 13[b] | 648 ± 231[b] | nd |
| DAS, 25 mg/kg 1 hour after APAP | 5/5 | 158 ± 41[c] | 2374 ± 3533[b] | nd |
| $DASO_2$, 25 mg/kg | 5/5 | 110 ± 70[c] | 1340 ± 1568[b] | 3–10% |
| N-AC, 300 mg/kg | 5/5 | 131 ± 68[c] | 1140 ± 96[b] | 10–17% |
| $DASO_2$, 25 mg/kg + N-AC, 300 | 5/5 | 140 ± 54[c] | 2452 ± 1503[b] | 7–22% |
| DAS, 25 mg/kg | 3/5 | 179 ± 2[c] | 15609 ± 7143[c] | 16–39% |

[a]Mice were fasted for 16 hours prior to administration of 0.2 g/kg of APAP and treated under conditions indicated. Values are expressed as the mean ± S.D. from survivors in duplicate determinations; nd, not determined. The dead animals were assigned with the highest enzyme activities.
[b-c]Means showing different superscripts in each column of each experiment are significantly different (p < 0.05) in the Newman-Keuls test.
[d]For purpose of comparison, extent of necrosis was graded by the criteria given in "Methods."

TABLE 4

Effects of $DASO_2$ Treatment on Acetaminophen Overdose in Mice[a]

| $DASO_2$ mg/kg | Treatment time (min) | Survival | GPT U/L | LDH U/L | Extent of liver damage |
|---|---|---|---|---|---|
| Control | | 5/5 | 45 ± 20[b] | 541 ± 140[b] | 0% |
| 0 | 0 | 3/5 | 200 ± 15[c] | 12384 ± 7923[c] | 33–42% |
| 5 | 0 | 5/5 | 51 ± 8[b] | 433 ± 98[b] | 3–5% |
| 25 | 0 | 5/5 | 84 ± 37[b] | 611 ± 252[b] | 5–10% |
| 50 | 0 | 5/5 | 79 ± 5[b] | 772 ± 138[b] | 4–9% |
| Control | 20 | 5/5 | 66 ± 8[b] | 647 ± 236[b] | nd |
| 0 | 20 | 2/5 | 208 ± 5[c] | 14904 ± 5477[c] | nd |
| 10 | 20 | 5/5 | 212 ± 1[c] | 16639 ± 8578[c] | nd |
| 25 | 20 | 5/5 | 89 ± 13[b] | 648 ± 231[b] | nd |

[a]Mice were fasted for 16 hours prior to administration of 0.2 g/kg of APAP and treated with various amounts of $DASO_2$ at indicated time after APAP treatment. Values are expressed as the mean ± S.D. from survivors in duplicate determinations. The dead animals were assigned with the highest enzyme activities.
[b-c]The means showing difference superscripts in each column of each experiment are significantly different (p < 0.05) in the Newman-Keuls test.

Figure 2A:
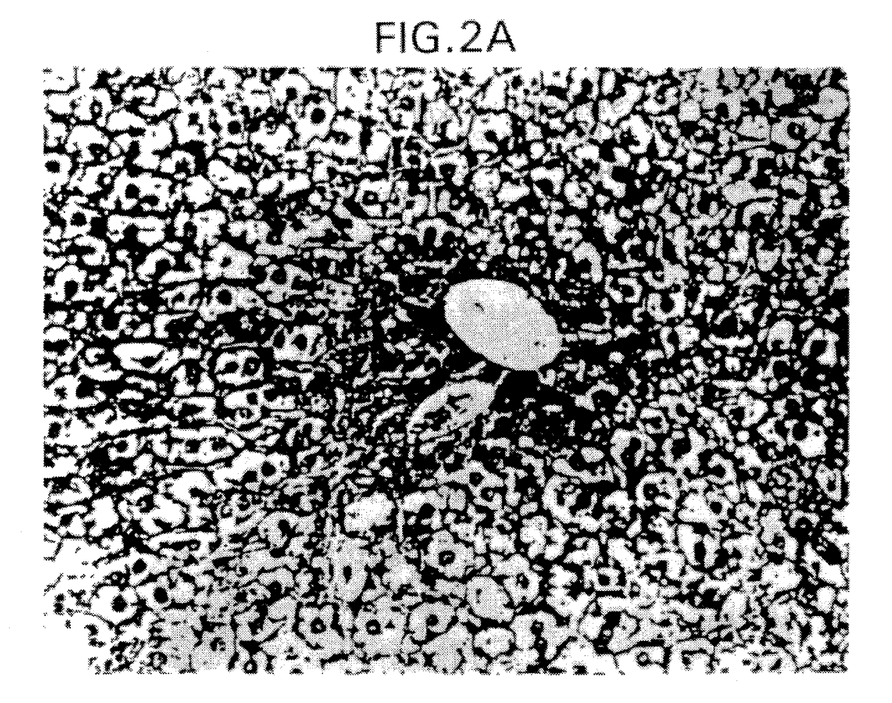
FIGS. 2A–2D are paraffin sections of liver stained with hematoxylin-eosin-phloxine, x400, illustrating the effects of $DASO_2$ on acetaminophen-induced hepatotoxicity in mice.
Figure 2B:
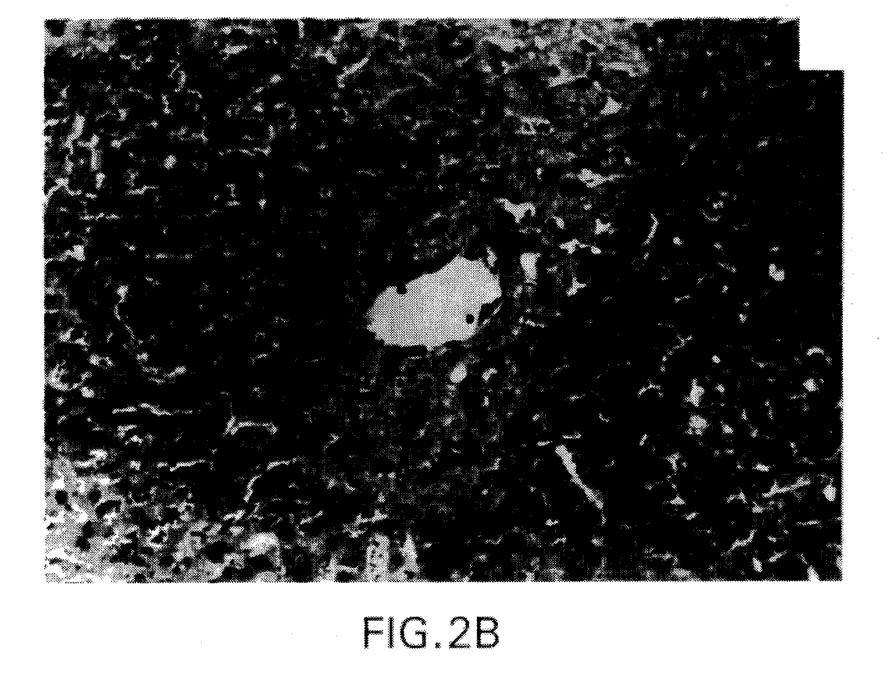
Figure 2C:
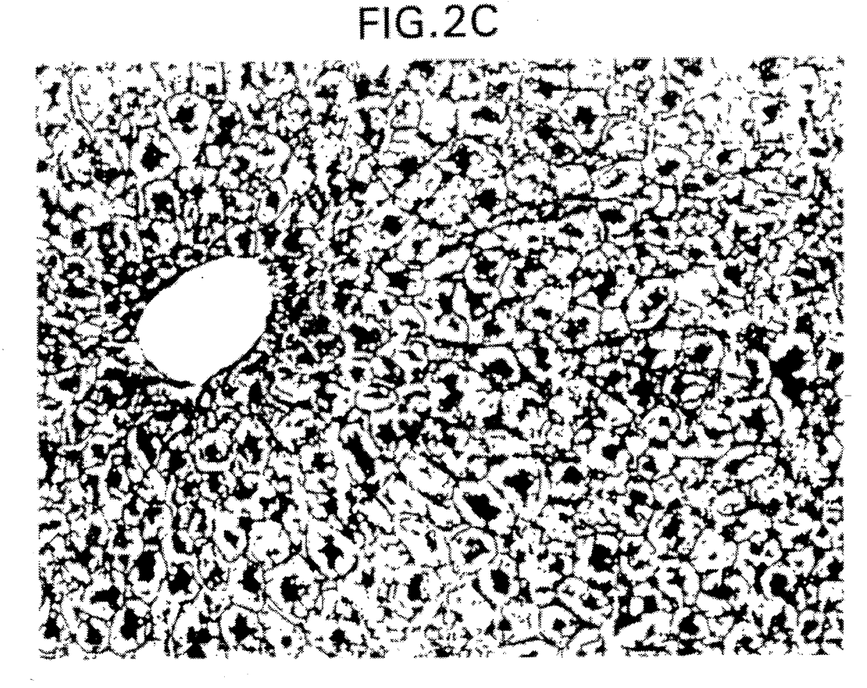
Figure 2D:
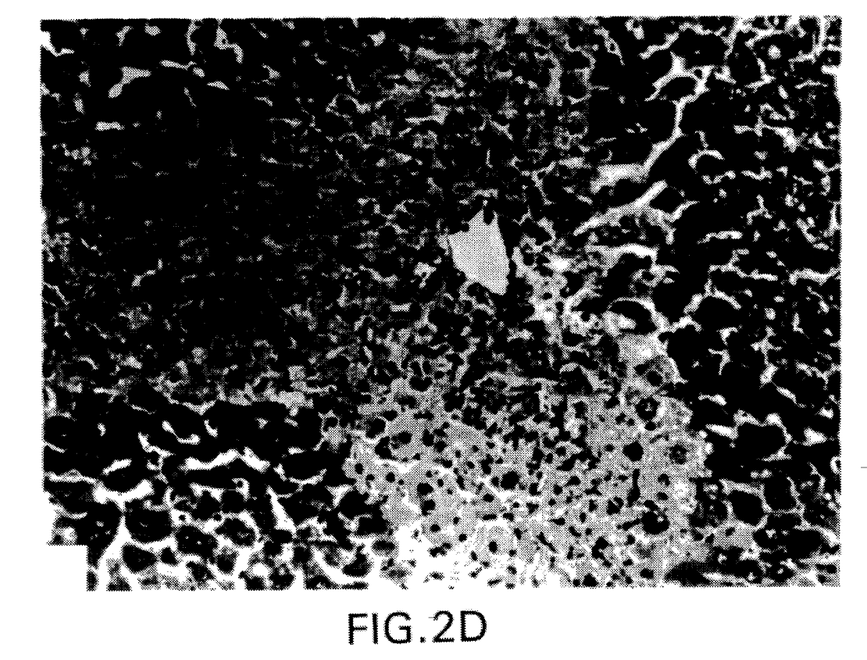

In FIGS. 2A–2D, paraffin sections of liver stained with hematoxylin-eosin-phloxine, x400, illustrate the effects of $DASO_2$ on acetaminophen overdose in mice. FIG. 2A illustrates a control liver. FIG. 2B is a liver section from a mouse given acetaminophen (0.2 g/kg), demonstrating hepatocellular necrosis. FIG. 2C, is a liver section from a mouse given $DASO_2$ (25 mg/kg) immediately after APAP (0.2 g/kg). FIG. 2D is a liver section from a mouse given $DASO_2$ (25 mg/kg) 1 hour after APAP (0.2 g/kg) treatment (Example 2h). Mice were killed 24 hours after receiving acetaminophen.

As can be ascertained from the experimental results detailed above, when mice were given acetaminophen (0.2 g/kg), there was a 40–60% mortality, severe liver damage, and highly elevated levels of serum GPT (5 fold increase) and LDH (20 fold increase). The histological evaluation of the livers of the surviving acetaminophen-treated mice showed typical centrilobular degeneration, necrosis, and inflammation (FIG. 2B). Livers from both control and $DASO_2$ treated mice appeared normal (FIGS. 2A, 2C). No increase of serum creatinine was observed in mice treated with up to 0.4 g/kg of acetaminophen.

The protective effect of $DASO_2$ was shown in Tables 3 and 4. When $DASO_2$ (25 mg/kg) was given either immediately or 20 minutes after acetaminophen (0.2 g/kg) dosing, it prevented mortality and the elevation of serum GPT and LDH levels as well as protected against liver damage based on histological evaluation (FIG. 2C). When given concomitantly with acetaminophen, 5 mg $DASO_2$/kg appeared to be sufficient to produce maximal protection; whereas 25 mg/kg was more effective than 10 mg/kg when $DASO_2$ was given 20 minutes after acetaminophen. $DASO_2$ (25 mg/kg) treatment at 1 hour after APAP dosing resulted in partial protection in preventing mortality, the elevation of serum LDH level, and the occurrence of severe liver damage (FIG. 2D, Table 2). However, serum GPT level elevation was not prevented.

As shown in Table 2, $DASO_2$ (25 mg/kg) and N-AC (300 mg/kg), as well as the combination of $DASO_2$ (25 mg/kg)

and N-AC (300 mg/kg), all protected against acetaminophen toxicity when given immediately after acetaminophen. Whereas, DAS (25 mg/kg), although preventing the elevation of the LDH level, only partially prevented liver damage and had little or no effect on the elevated serum GPT level. When given 1 hour after acetaminophen dosing, $DASO_2$ (25 mg/kg), N-AC (300 mg/kg), and the combination of $DASO_2$ and N-AC all showed partial protection against hepatotoxicity as judged by mortality, LDH level, and the extent of liver injury. When given 3 hours after acetaminophen dosing, neither $DASO_2$, N-AC nor the combination treatment was effective (data not shown).

EXAMPLE 3

Modulation of P-450 Activities by $DASO_2$

Previous work indicated that rats treated with $DASO_2$ (200 mg/kg) showed a marked decrease of liver microsomal N-nitrosodimethylamine (NDMA) demethylase activity. In Example 3, this effect was studied in mice. In Example 3, changes in hepatic monooxygenase enzymes after a single oral dose of $DASO_2$ were studied. $DASO_2$ (50 mg/kg) was administered to mice intragastrically and sacrificed at the indicated time. Control (0 time) mice received distilled water only.

Figure 3:
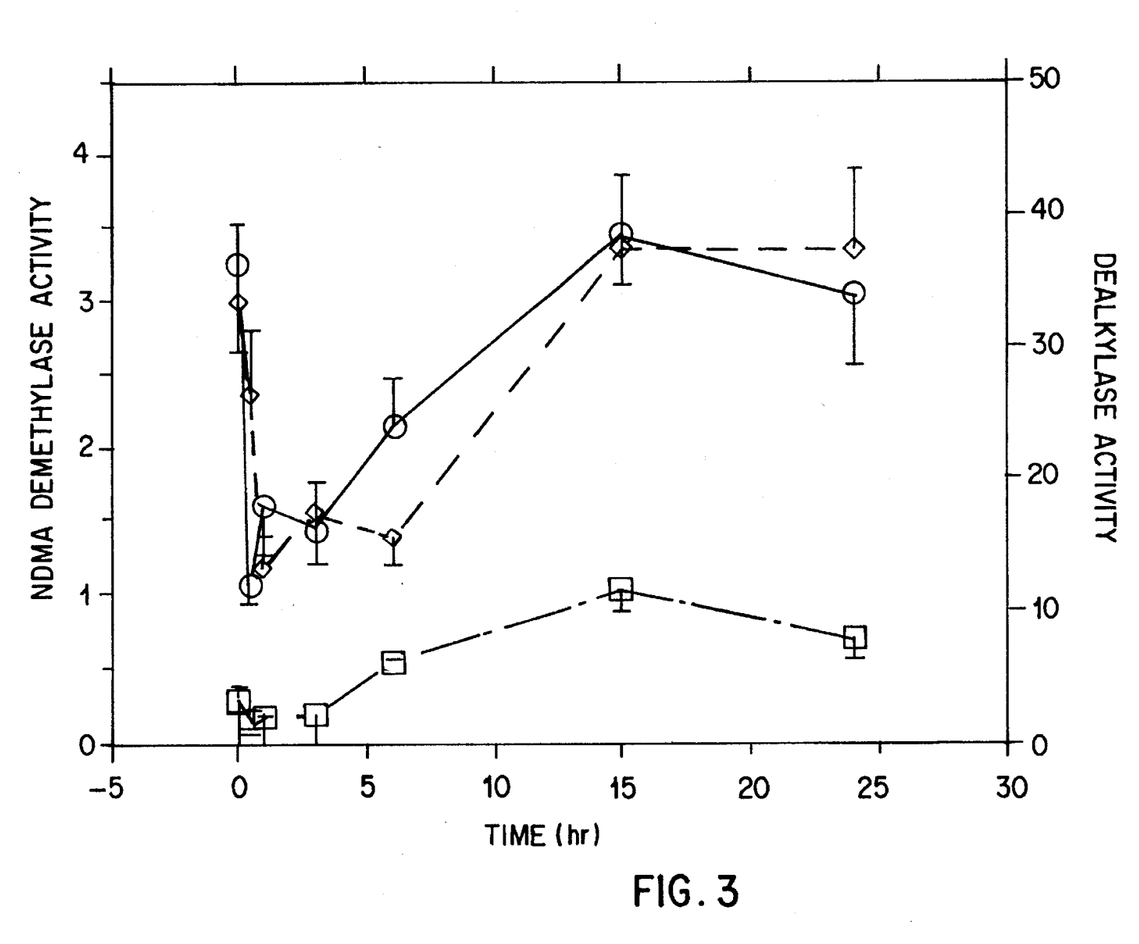
FIG. 3 is a graphical representation of the modulation of Cytochrome P-450 enzyme activities by $DASO_2$.

The results are shown in FIG. 3. Hepatic microsomal NDMA demethylase activity (O) is expressed as nmol HCHO produced/min/mg. Pentoxyresorufin ([ ]) and ethoxyresorufin ($\Diamond$) dealkylase activities are expressed as pmol resorufin produced/min/mg. Each point represents the mean $\pm$S.D. of five separate microsomal preparations. *$p<0.05$ compared to control.

As shown in FIG. 3, a single oral dose of 50 mg/kg $DASO_2$ decreased P-450 2E1-dependent NDMA demethylase activity to 31%, 54%, 49%, and 73% of the control level after 0.5, 1, 3, and 6 hours, respectively. P-450 1A2 dependent ethoxyresorufin (EORR) dealkylase activity (Bourdi et al., "A new Anti-Liver Endoplasmic Reticulum Antibody Directed Against Human Cytochoursome P-450 1A2; A Specific Marker of Dihydralazine-Induced Hepatitis, J. Clin. Invest. 85:1967–1973 (1990)) also decreased to 79%, 39%, 52%, and 46% of control level, respectively.

The results suggest that $DASO_2$ not only decreased the activity of P-450 2E1, but may also decrease P-450 1A2 activity. Both NDMA demethylase and EORR dealkylase activities returned to control levels after 15 hours. There was no significant change in pentoxyresorufin (PORR) dealkylase activity.

EXAMPLE 4

Dose-Dependent and Competitive Inhibition of APAP Bioactivation by $DASO_2$

In Example 4, the effect of $DASO_2$ concentration on acetaminophen metabolic activity was studied. Acetaminophen metabolic activity in ethanol-treated rat liver microsomes, measured as N-acetyl-p-benzoquinone imine-glutathione conjugate (NAPQI-GSH) formation, was determined as follows.

Ethanol-induced rat liver microsomes from male Sprague-Dawley rats were prepared as described in Peng et al., "The Induction and Competitive Inhibition of a High Affinity Microsomal Nitrosodimethylamine Demethylase by Ethanol", Carcinogenesis (Lond.), 3:1457–1461 (1982). The reaction mixture contained microsomes (0.4 mg protein), 50 µM of acetaminophen, 10 mM of glutathione, an NADPH generating system (0.4 mM of NADP, 10 mM of glucose 6-phosphate, and 0.5 unit of glucose-6-phosphate dehydrogenase), 3 mM $MgCl_2$, and potassium phosphate (50 µM, pH 7.4) in a final volume of 1 ml. After incubation at 37° C. for 30 minutes, the reactions were terminated by the addition of 3% ice-cold sulfosalicylic acid. The protein was removed by centrifugation and the resulting supernatant was analyzed for NAPQI-GSH formation by High-Pressure Liquid Chromatography (HPLC). For immuno-inhibition studies, the microsomes were pre-incubated with antibodies at 4° C. for 15 minutes before the enzyme assay.

Quantitative determination of the glutathione and NAPQI conjugates was carried out by a modification of the method of Hu et al., "Sex-Related Differences in Mouse Renal Cytochrome P450IIE1: Effects on the Metabolism and Nephrotoxicity of Acetaminophen", FASEB J 5:1565 (1991), based on the method described by Buckpitt et al., "Quantitative Determination of the Glutathione, Cysteine, and N-acetyl Cysteine Conjugates of Acetaminophen By High-Pressure Liquid Chromatography, Anal. Biochem., 83:168–177 (1977). A Waters Model 490E high-performance liquid chromatograph (Waters Assoc., Milford, Mass.) equipped with a Waters Model 460 electrochemical detector was used. Separations were performed on a 15 cm×4.6 mm ID (5 micron) Supelcosil LC-18 column (Supelco, Inc., Bellefonts, Pa.). The mobile phase was 9.4% methanol and 0.08% tetrafluoroacetic acid and the flow rate was 2 ml/min. Free acetaminophen and NAPQI-GSH conjugate were eluted at 3.5 and 10 min. respectively. The quantity of NAPQI-GSH was determined using a $^3$H-labeled NAPQI-GSH standard.

Figure 4:
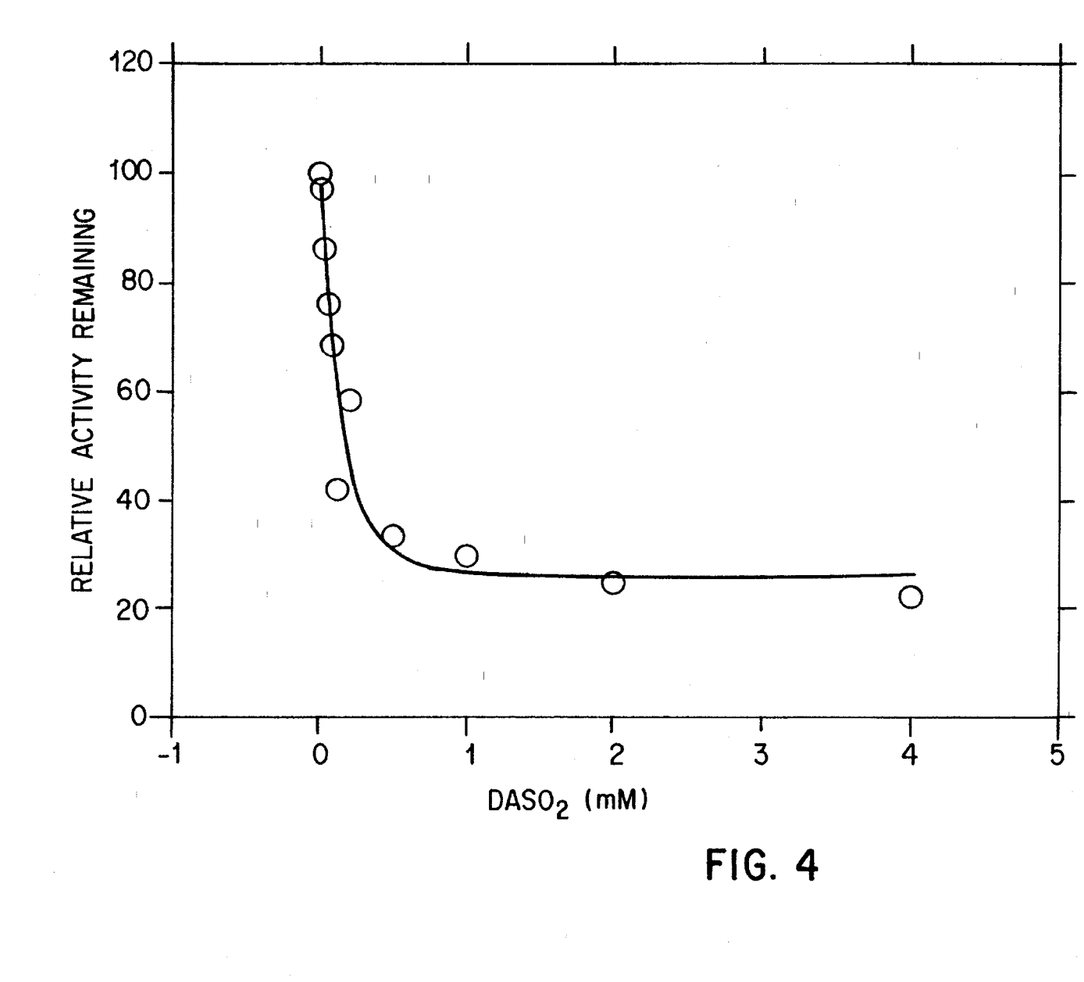
FIG. 4 is a graphical representation of the dose-dependent manner in which $DASO_2$ inhibits acetaminophen bioactivation.

As shown in FIG. 4, $DASO_2$ inhibited acetaminophen bioactivation in a dose-dependent manner. The rate of NAPQI-GSH production from acetaminophen was inhibited by 77% by 1 mM of $DASO_2$. The relative activity remaining represents the % of activity compared to the activity (0.80 nmol/min/mg) in the absence of $DASO_2$.

EXAMPLES 5–6

Formulations

In Example 5, compositions for treating acetaminophen overdose are manufactured.

In Example 5a, tablets and capsules of diallyl sulfone are prepared. The tablets and capsules are formulated to a pharmaceutically acceptable size for oral intake, such that the dose contains, e.g., a dose of 350 mg diallyl sulfone. Inert pharmaceutical excipients are added as needed. Multiple tablets or capsules may be taken by the patient who has ingested a toxic dose of acetaminophen. The amount of diallyl sulfone taken may be determined based upon the amount of acetaminophen ingested (if known), or may be based upon the patient's body weight and the desired dose (e.g., from about 5 mg/kg body weight to about 50 mg/kg body weight).

Example 5b is prepared in similar fashion to Example 6a, except that diallyl sulfide is included instead of diallyl sulfone. The amount of diallyl sulfone taken may be determined based upon the amount of acetaminophen ingested (if known), or may be based upon the patient's body weight and the desired dose (e.g., from about 25 mg/kg body weight to about 100 mg/kg body weight).

In Example 5c, oral liquid dosage forms of the diallyl sulfide and diallyl sulfone are prepared.

In Example 5d, an effective amount of N-acetylcysteine to detoxify the hepatotoxic metabolites of acetaminophen is added to each of the compositions of Examples 5a, 5b, and 5c. The total amount of N-acetylcysteine to be taken by the patient who has ingested a toxic amount of acetaminophen is preferably from about 50 mg/kg to about 140 mg/kg body weight. The final products of Examples 5a–5c preferably contain a proportionate amount of N-acetylcysteine such that when, for example, multiple tablets are taken by the patient to obtain the desired dosage of diallyl-sulfone, the patient also is given a desired dose of N-acetylcysteine.

In Example 6, compositions containing a pharmaceutically acceptable unit dose(s) of acetaminophen, and further containing diallyl sulfone (with or without N-acetylcysteine) are manufactured.

In Example 6a, diallyl sulfone in a ratio of from about 1:4 to about 1:80 is added to a pharmaceutically acceptable unit dose of acetaminophen, e.g., 325 mg acetaminophen. The amount of diallyl sulfone added to the formulation is, e.g., from about 4.06 mg (ratio=1:80) to about 81.25 (ratio=1:4). Suitable pharmaceutically acceptable inert excipients are added as needed. The mixture may be wet granulated and thereafter compressed into tablets of a pharmaceutically acceptable size. On the other hand, the formulation may be encapsulated in hard gelatin capsules.

The final product may prepared in any desired commercially available form of acetaminophen, e.g., capsules, elixirs, oral solutions, oral suspensions, drops, syrups, wafers, tablets, chewable tablets, caplets, suppositories, and buffered effervescent granules. Acetaminophen formulations are well-known in the art, and may be readily adapted to incorporate diallyl sulfone. For example, a wet granulation method for preparing 300 mg acetaminophen tablets is provided in detail in *Remingtons's Pharmaceutical Sciences* (Arthur Oxol, editor), page 1572 (1980). Acetaminophen formulations comprising diallyl sulfone may be preferable, because diallyl sulfide has an odor.

In Example 6b, an effective amount of N-acetylcysteine to detoxify the hepatotoxic metabolites of acetaminophen is added to the compositions of Examples 6a. The amount of N-acetylcysteine included in the formulation is preferably an effective amount to detoxify the hepatotoxic metabolites of acetaminophen should a patient ingest a potentially hepatotoxic number of unit doses of acetaminophen.

The formulations of Examples 6a and 6b include oral solid dosage forms comprising a unit dose of acetaminophen of 80 mg, 325 mg, 500 mg, and 650 mg; oral liquid dosage forms comprising acetaminophen in concentrations of 100 mg/ml, 120 mg/2.5 ml, 120 mg/5 ml, 160 mg/5 ml, 165 mg/5 ml, and 325 mg/5 ml; effervescent granules comprising a unit dose of 325 mg acetaminophen; and suppositories comprising a unit dose of 120 mg, 125 mg, 325 mg, and 650 mg acetaminophen. In the formulation comprising 500 mg acetaminophen, for example, 0.01–10 mg of $DASO_2$ is included.

The examples provided above are not meant to be exclusive. Many other variations of the present invention would be obvious to those skilled in the art, and are contemplated to be within the scope of the appended claims. The publications cited above are all hereby incorporated by reference.

What is claimed is:

1. A method of treating acetaminophen overdose in a patient who has ingested an hepatotoxic dose of acetaminophen, comprising administering a protective agent comprising diallyl sulfone in an amount effective to prevent the metabolism of the ingested dose of acetaminophen into its hepatotoxic metabolites.

2. The method of claim 1, comprising administering said protective agent within about 24 hours after the acetaminophen dose has been ingested.

3. The method of claim 1, comprising administering said protective agent within about 6 hours after the acetaminophen dose has been ingested.

4. The method of claim 1, further comprising concomitantly administering with said protective agent an effective amount of a detoxifying agent selected from the group consisting of N-acetylcysteine, L-methionine, L-cysteine, and mixtures thereof to detoxify the hepatotoxic metabolites of acetaminophen.

5. The method of claim 1, comprising orally administering said protective agent.

6. The method of claim 4, wherein diallyl sulfone and N-acetylcysteine are administered.

7. The method of claim 1, comprising administering diallyl sulfone in an amount from about 0.04 mg/kg/day to about 50 mg/kg/day, based on the weight of the patient.

8. A method for treating acetaminophen overdose in a patient who has ingested an hepatotoxic dose of acetaminophen, comprising administering a protective agent comprising diallyl sulfone in an effective amount to substantially prevent the cytochrome P-450 2E1 induced metabolism of the ingested dose of acetaminophen to N-acetyl-p-benzoquinone imine.

9. The method of claim 8, wherein said protective agent further comprises N-acetylcysteine in an amount effective to detoxify hepatotoxic metabolites of acetaminophen.

10. The method of claim 8, comprising administering said protective agent intravenously.

11. The method of claim 8, comprising administering said formulation in an oral dosage form.

12. The method of claim 9, comprising administering said formulation in an oral dosage form.

13. The method of claim 8, comprising administering from about 0.1 mg/kg/day to about 100 mg/kg/day of diallyl sulfone, based on patient weight.

14. The method of claim 8, further comprising administering an effective amount of a detoxifying agent selected from the group consisting of N-acetylcysteine, L-methionine, L-cysteine, and mixtures thereof to detoxify the hepatotoxic metabolites of acetaminophen.

15. A method for the treatment of pain or fever with acetaminophen which prevents the formation of hepatotoxic metabolites of acetaminophen in the event that a patient is exposed to an otherwise hepatotoxic overdose of acetaminophen, comprising administering to a human as a unit dose a therapeutically effective amount of acetaminophen together with a protective agent comprising diallyl sulfone in an effective amount to substantially inhibit the metabolism of the therapeutically effective amount of acetaminophen into a hepatotoxic metabolite.

16. An oral dosage form for treating an hepatotoxic overdose of acetaminophen, comprising a pharmaceutically acceptable unit dose of acetaminophen and a protective agent comprising diallyl sulfone in a pharmaceutically acceptable amount effective to prevent the metabolism of at least a portion of an ingested dose of acetaminophen into its hepatotoxic metabolites.

17. The composition of claim 16, further comprising an effective amount of a detoxifying agent selected from the group consisting of N-acetylcysteine, L-methionine, L-cysteine, and mixtures thereof to detoxify the hepatotoxic metabolites of acetaminophen.

18. The composition of claim 17, wherein the detoxifying agent is N-acetylcysteine.

19. The composition of claim 17 which is in a dosage form selected from the group consisting of capsules, elixers, oral solutions, oral suspensions, drops, syrups, wafers, tablets, chewable tablets, caplets, suppositories, and buffered effervescent granules.

20. An oral dosage form, comprising a pharmaceutically acceptable unit dose of acetaminophen, and a protective agent comprising diallyl sulfone in an amount effective to prevent the metabolism of said unit dose of acetaminophen into its hepatotoxic metabolites.

21. The composition of claim 20, further comprising an effective amount of a detoxifying agent selected from the group consisting of N-acetylcysteine, L-methionine, L-cysteine, and mixtures thereof to detoxify the hepatotoxic metabolites of acetaminophen.

22. The composition of claim 21, wherein the detoxifying agent is N-acetylcysteine.

23. The composition of claim 20 which is an oral solid dosage form comprising a unit dose of acetaminophen selected from the group consisting of 80 mg, 325 mg, 500 mg, and 650 mg.

24. The composition of claim 20 which is an oral liquid dosage form comprising acetaminophen in a concentration selected from the group consisting of 100 mg/ml, 120 mg/2.5 ml, 120 mg/5 ml, 160 mg/5 ml, 165 mg/5 ml, and 325 mg/5 ml.

25. The composition of claim 20, further comprising an active ingredient selected from the group consisting of a decongestant, a bronchodilator, an antitussive agent, an antihistamine, a muscle relaxant, and a combination of any of the foregoing.

* * * * *